US00PP29342P2

(12) United States Plant Patent
van Langen

(10) Patent No.: US PP29,342 P2
(45) Date of Patent: May 29, 2018

(54) ***ECHEVERIA* PLANT NAMED 'AMIECH1618'**

(50) Latin Name: *Echeveria agavoides*
Varietal Denomination: AMIECH1618

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days. days.

(21) Appl. No.: 15/530,485

(22) Filed: Jan. 20, 2017

(51) Int. Cl.
*A01H 5/02* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Echeveria agavoides* cultivar named 'AMIECH1618' which is characterized by thick, succulent foliage with an upwardly curved attitude, and foliage that is tightly arranged in a compact rosette, particularly at the center of the rosette. The broad ovate to near oblong foliage is lightly pruinose with a greyed-green general coloration, leaf margins which are lightly suffused with red-purple, a prominent red coloration of the leaf apex, and the stability of these characteristics from generation to generation.

4 Drawing Sheets

Latin name of the genus and species: The Latin name of the genus and species of the novel variety disclosed herein is *Echeveria agavoides.*

Variety denomination: The inventive variety of *Echeveria* disclosed herein has been given the variety denomination 'AMIECH1618'.

BACKGROUND OF THE INVENTION

Parentage: 'AMIECH1618' is a seedling selection resulting from the self-pollination of the species, *Echeveria agavoides* (unnamed). The crossing was made by the inventor in the spring of 2010 at a commercial greenhouse in Heerhugowaard, the Netherlands. Seed from said cross was harvested, then germinated, and the resulting seedlings were then grown to a mature size. In summer of 2011, one seedling was observed to exhibit unique foliage characteristics and growth habit. The seedling was isolated for further evaluation in order to confirm the distinctness and stability of the characteristics first observed. Upon confirmation of distinctness and stability, 'AMIECH1618' was selected for commercialization in the summer of 2012.

Asexual Reproduction: Asexual reproduction of the new cultivar 'AMIECH1618', by way of rooting leaf cuttings, was first initiated in the summer of 2013 at the inventor's commercial greenhouse in Heerhugowaard, the Netherlands. Through six subsequent generations, the unique features of this cultivar have proven to be stable and true to type.

SUMMARY OF THE INVENTION

The cultivar 'AMIECH1618' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1618'. These characteristics in combination distinguish 'AMIECH1618' as a new and distinct *Echeveria agavoides* cultivar:

1. 'AMIECH1618' exhibits thick, succulent foliage with an upwardly curved attitude;
2. 'AMIECH1618' exhibits foliage tightly arranged into a compact rosette, particularly at the center of the rosette; and
3. 'AMIECH1618' exhibits broad ovate to near oblong foliage with a short apiculate apex; and
4. 'AMIECH1618' exhibits lightly pruinose foliage with a greyed-green general coloration, margins which are lightly suffused with red-purple, and a red apex.

BOTANICAL DESCRIPTION OF THE PLANT

Figure 1:
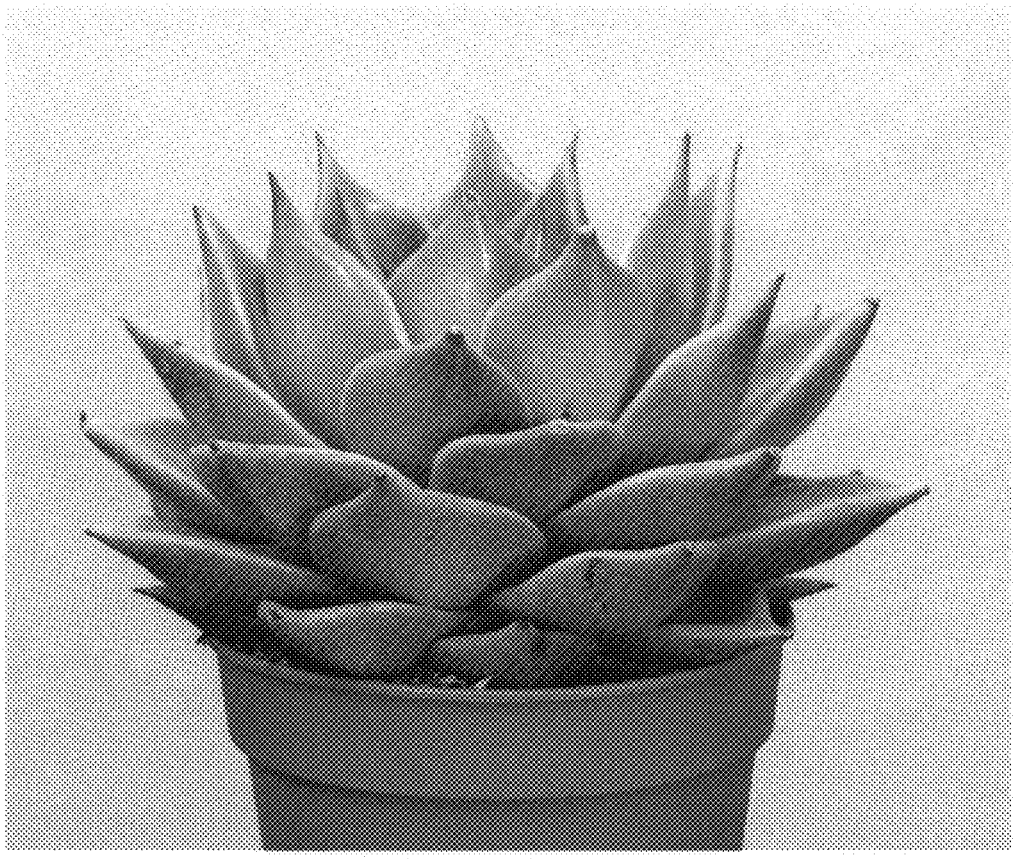
FIG. 1 illustrates, as nearly true as it is reasonably possible to make the same in color photographs of this type, an exemplary plant of 'AMIECH1618' grown in a commercial greenhouse in Heerhugowaard, the Netherlands. This plant is approximately 9 months old, shown planted in a 12 cm container.
Figure 2:
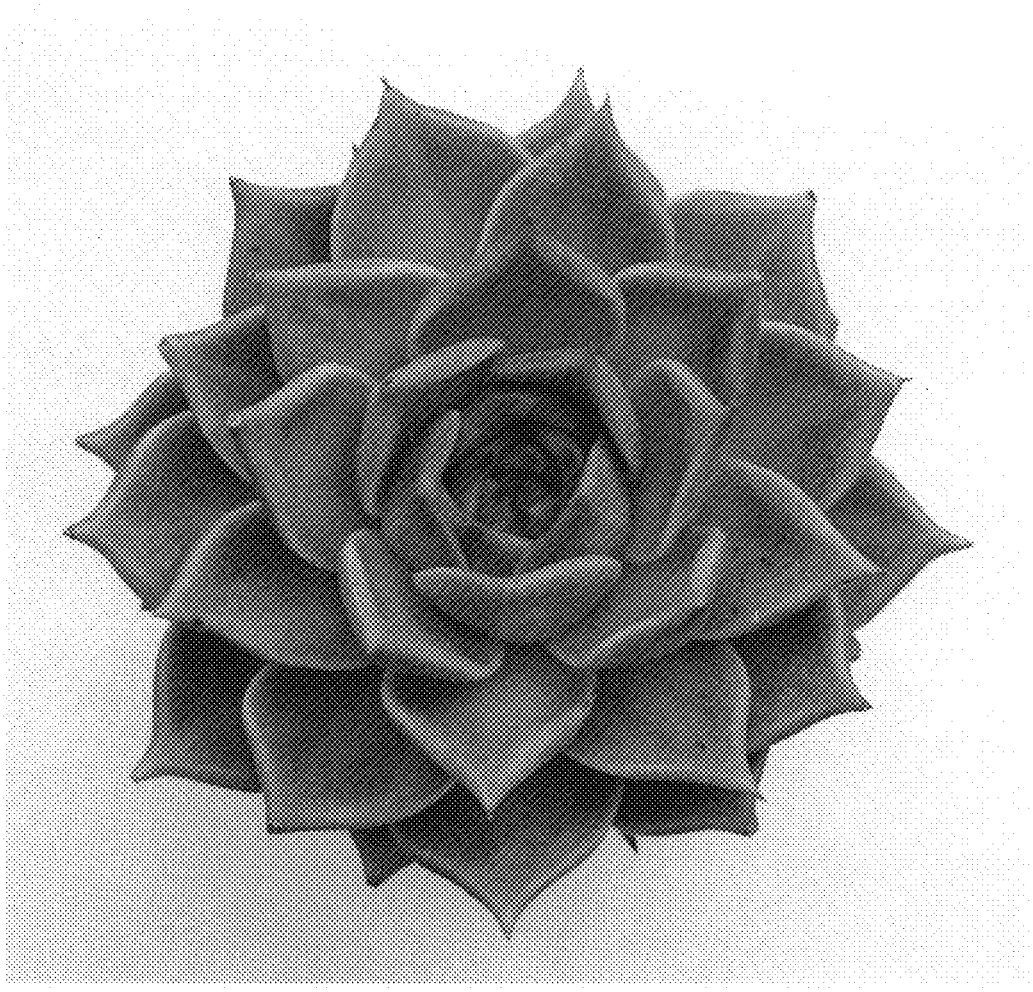
FIG. 2 illustrates, as nearly true as it is reasonably possible to make the same in color photographs of this type, the typical foliage arrangement of 'AMIECH1618'.
Figure 3:
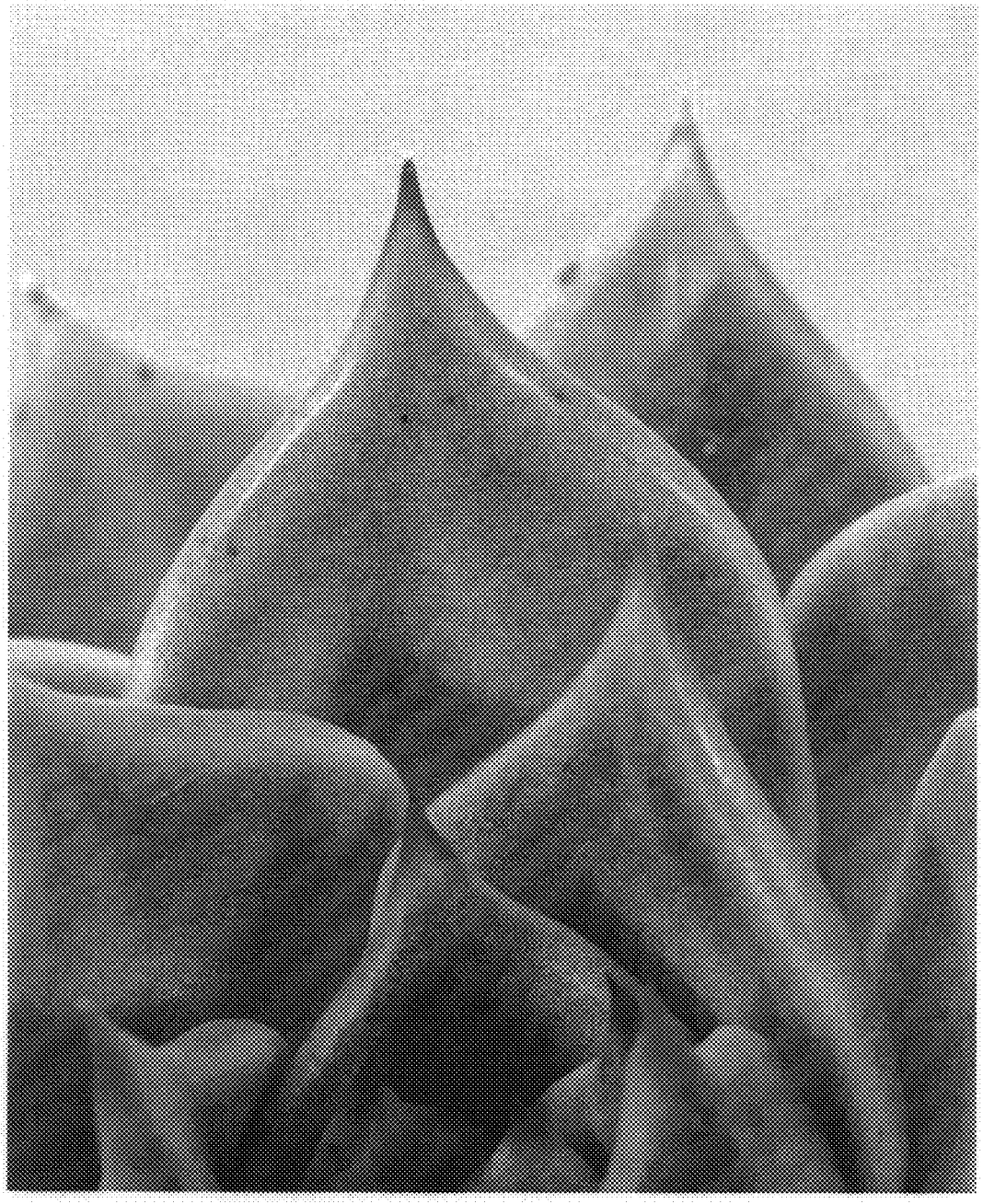
FIG. 3 illustrates, as nearly true as it is reasonably possible to make the same in color photographs of this type, the foliage color from the center of the rosette (juvenile foliage) to the outer most whorl of the rosette (mature foliage) of 'AMIECH1618'.
Figure 4:
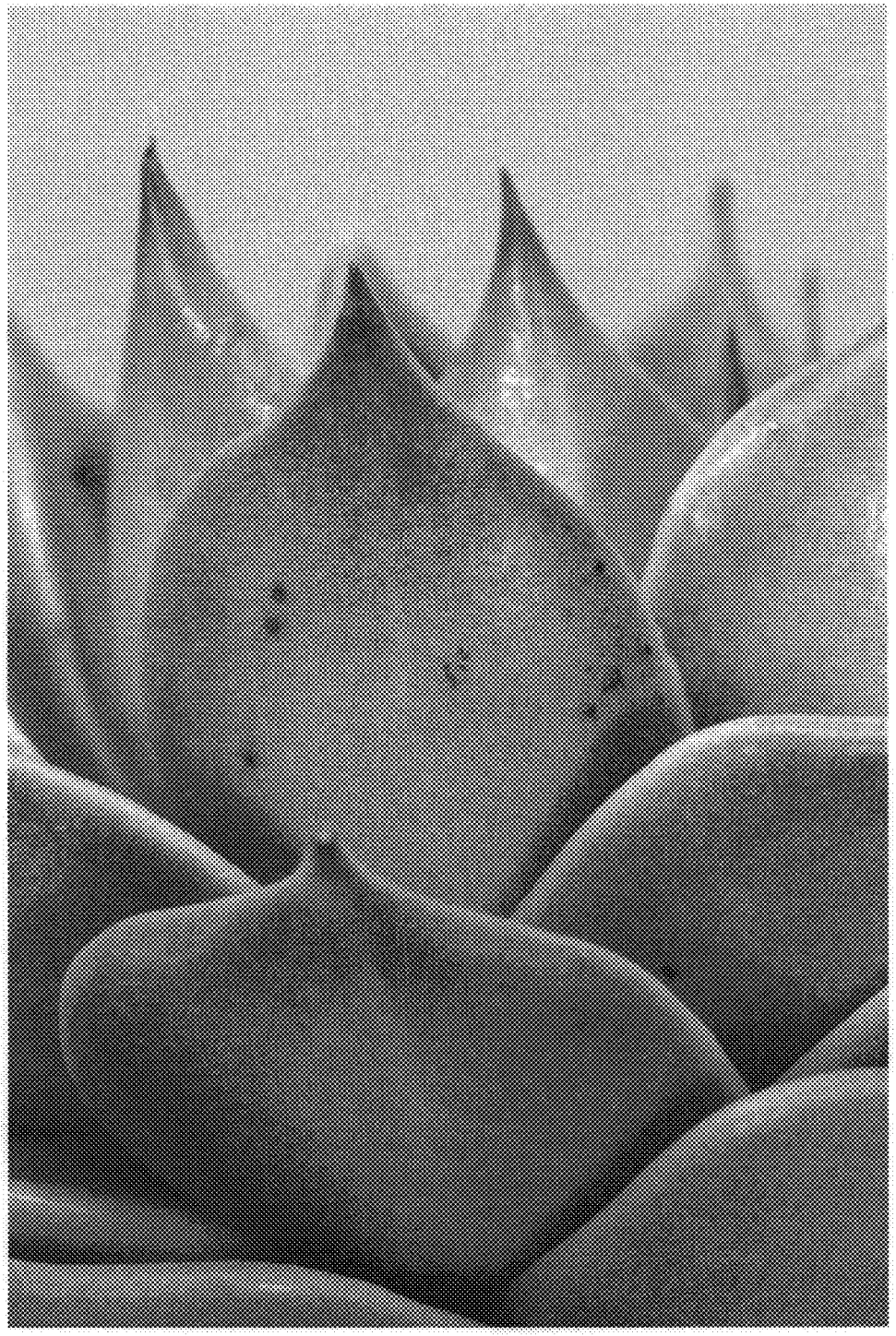
FIG. 4 illustrates, as nearly true as it is reasonably possible to make the same in color photographs of this type, the abaxial surface of the mature foliage 'AMIECH1618'.

The following observations and measurements made in October of 2016 describe averages from a sample set of six specimens of 9 months old 'AMIECH1618' plants grown in 12 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1618' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1618' and a comparison with the parent and closest known comparator, *Echeveria agavoides*, is provided below.

Plant description:

*Growth habit*.—Succulent perennial with foliage growing in a non-branched basal rosette.

*Plant shape*.—Flattened globular.

*Height from soil level to top of foliar plane*.—10.6 cm.

*Plant spread*.—Average of 18.0 cm.

*Growth rate*.—Moderate.

*Plant vigor*.—Moderate.

*Propagation*.—Type — Leaf cuttings. Time to initiate rooting — Approximately 21 to 35 days at 18 degrees Celsius. Crop time — Approximately 18 to 22 weeks to produce a marketable plant in an 11 cm container.

*Disease and pest resistance or susceptibility*.—Neither resistance nor susceptibility to typical *Echeveria agavoides* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 48 leaves per rosette.

*Shape*.—Thick, succulent leaves which are obovate to near oblong.

*Dimensions*.—7.8 cm long, 4.5 cm wide, and 1.5 cm thick, on average.

*Aspect*.—Slightly concave and slightly carinate.

*Apex*.—Short apiculate.

*Base*.—Broad cuneate.

*Margin*.—Entire; not undulated or lobed.

*Pubescence, texture and luster of the adaxial surface*.—Glabrous, smooth, and moderately glossy; lightly pruinose.

*Pubescence, texture and luster of the abaxial surface*.—Glabrous, smooth, and moderately glossy; lightly pruinose.

*Color*.—Juvenile foliage, adaxial surface — Greyed-green, nearest to RHS 191A; apex is greyed-purple, RHS 185B. Juvenile foliage, abaxial surface — Greyed-green, nearest to RHS 193A; apex is greyed-purple, in between RHS 185A and 185B. Mature foliage, adaxial surface — Yellow-green, nearest to RHS 147C, and suffused with green towards the apex, nearest to RHS NN137D; apex is greyed-purple, RHS 185B. Mature foliage, abaxial surface — Yellow-green, nearest to RHS 147C, and suffused with greyed-green towards the apex, nearest to RHS 191A; apex is greyed-purple, RHS 185B.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1618' differ from the parent, *Echeveria agavoides*, which is also the closest known comparator, in the following characteristics described in Table 1 below.

TABLE 1

| Characteristic | 'AMIECH1618' | *Echeveria agavoides* |
|---|---|---|
| Leaf attitude, outer whorls of the rosette. | More erect. | More relaxed. |
| Leaf width. | Wider than the parent. | Narrower than 'AMIECH1618'. |
| Leaf thickness. | Thicker than the parent. | Thinner than 'AMIECH1618'. |
| Leaf apex. | Short apiculate. | Acute. |
| General coloration of mature foliage, | Greyed-green with prominent red coloration of the apex. | Yellow-green with less prominent red coloration of the apex. |

That which is claimed is:

1. A new and distinct variety of *Echeveria agavoides* plant named 'AMIECH1618', substantially as described and illustrated herein.

* * * * *